(12) United States Patent
Shihadeh

(10) Patent No.: US 6,494,097 B1
(45) Date of Patent: Dec. 17, 2002

(54) METHOD AND APPARATUS FOR MEASURING THICKNESS OF A LAYER IN A MULTI-LAYERED OBJECT

(76) Inventor: Elias Edmond Shihadeh, 5053-6 (El Meteran) Street, P.O. Box 8881, Nazareth 16000 (IL)

( * ) Notice: Subject to any disclaimer, the term of this patent is extended or adjusted under 35 U.S.C. 154(b) by 87 days.

(21) Appl. No.: 09/654,884

(22) Filed: Sep. 5, 2000

(51) Int. Cl.⁷ .............................................. G01N 29/04
(52) U.S. Cl. ........................................ 73/602; 600/438
(58) Field of Search ........................ 73/588, 597, 579, 73/599, 602, 606, 609, 620, 628, 627, 629, 598, 631, 642; 600/587, 438, 439, 442, 2

(56) References Cited

U.S. PATENT DOCUMENTS

| | | | |
|---|---|---|---|
| 5,038,615 A | * 8/1991 | Trulson et al. ................ | 73/597 |
| 5,197,019 A | 3/1993 | Delon-Martin et al. ..... | 364/563 |
| 5,303,590 A | * 4/1994 | Modderman et al. ......... | 73/588 |
| 5,351,544 A | 10/1994 | Endo et al. .................... | 73/588 |
| 5,663,502 A | * 9/1997 | Nagashima et al. .......... | 73/599 |
| 5,806,520 A | 9/1998 | Berger et al. .......... | 128/660.06 |
| 5,866,819 A | * 2/1999 | Albu et al. .................... | 73/629 |
| 5,908,388 A | * 6/1999 | Watkin et al. ............... | 600/438 |
| 5,974,886 A | 11/1999 | Carroll et al. ................ | 73/598 |
| 6,250,159 B1 | * 6/2001 | Kreier et al. ................. | 73/602 |

FOREIGN PATENT DOCUMENTS

| | | | |
|---|---|---|---|
| DE | 3425811 | | 3/1985 |
| JP | 63-221211 | * | 9/1988 |
| JP | 6-3000550 | * | 10/1994 |

* cited by examiner

Primary Examiner—Helen Kwok
(74) Attorney, Agent, or Firm—Gary M. Nath; Todd L. Juneau; Joshua B. Goldberg

(57) ABSTRACT

A method and device for determining a thickness of a layer in an object. For each of a plurality of frequencies, a continuous vibrational wave is generated at a surface of the layer and an energy of a steady state echo wave produced in the object in response to the generated vibrational wave is measured. The thickness of the layer is then calculated based upon the measured energies of the steady state echoes.

16 Claims, 2 Drawing Sheets

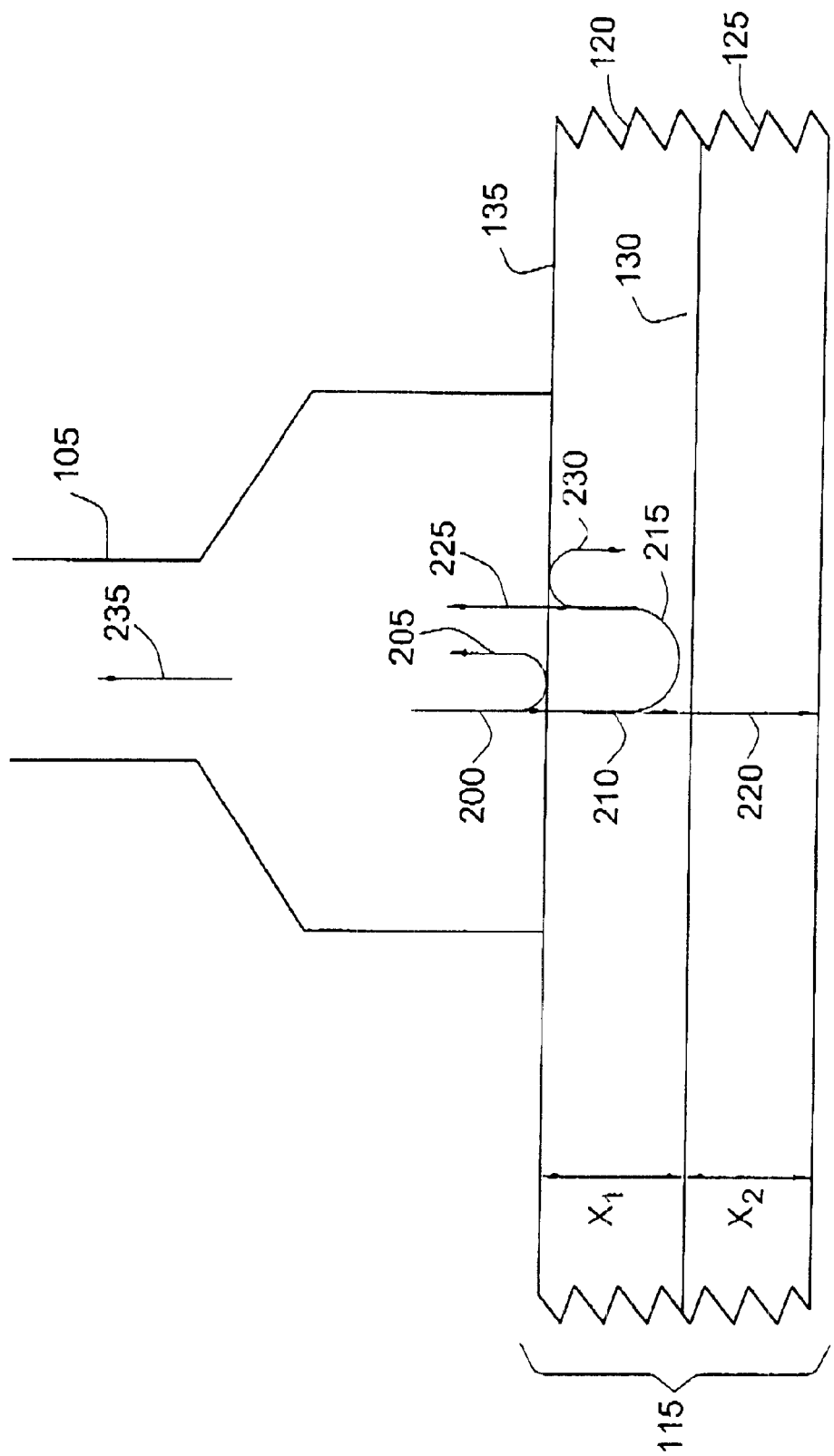

METHOD AND APPARATUS FOR MEASURING THICKNESS OF A LAYER IN A MULTI-LAYERED OBJECT

FIELD OF THE INVENTION

The present invention relates to methods for measuring the thickness of a layer in a multi-layered object.

BACKGROUND OF THE INVENTION

There are several prior art devices for measuring the thickness of a layer in multi-layer materials.

U.S. Pat. Nos. 5,974,886 and 5,197,019 disclose a method in which a short pulse vibration generated by a transducer is directed to the material. Each interface between adjacent layers generates an echo that arrives at a detector transducer at different times. The thickness of a layer is calculated as the time difference between the two echoes formed at the two surfaces of the layer multiplied by the sound velocity in the layer. However, for thin layers the time between the echoes is very small, and any error in the time measurement leads to a corresponding error in the thickness. In addition, a crystal transducer usually has several lobes, (a main lobe and side lobes) and the pulse echo of the side lobes will be superimposed on the main pulse echoes and will thus add noise to the measurement.

Another method known in the art involves submerging the material in a coupler liquid and obtaining the frequency spectrum of the material, for example, as described in U.S. Pat. No. 5.351,544. This however cannot be used for in vivo measurement since it is impractical to introduce a coupler liquid into the body. U.S. Pat. No. 5,806,520 discloses a method for determining the thickness of bone, but this method is not accurate for hidden or hard to access tissues, or layers of small thickness.

SUMMARY OF THE INVENTION

The present invention provides an apparatus and method for measuring the thickness of hidden or hard to access layers in a multi-layer structure.

In accordance with the inventions an input vibrational wave is transmitted to the surface of the structure by means of a probe. The steady state echo of the input wave is the superimposition of a series of echoes formed at the front and back surfaces of the layer. The steady state echo is transmitted from the structure to a detector through the probe that determines the energy of the steady state echo and stores it in a memory. The frequency of the generated wave is varied, and the energy of the steady state echo at each frequency is determined and stored in the memory. As described in detail below, the thickness of the layer is then calculated from frequencies at which the intensity of the steady state echo is minimal. The invention may be used to determine the thickness of a layer in an organism. For example, the invention may be used to determine the thickness of a bone.

The invention allows non-invasive measurement of a layer thickness and may therefore be used in medical imaging procedures. The invention may be used to measure the thickness of hidden or difficult to access structures, such as bone or arteriosclerosis in an artery.

Thus, in its first aspect, the invention provides a method for determining a thickness $x_1$ of a layer in an object, the method comprising the steps of:
(a) for each of a plurality of frequencies $f_1, \ldots f_k$
  (aa) generating a continuous vibrational wave at a surface of the layer;
  (ab) measuring an energy of a steady state echo wave produced in the object in response to the generated vibrational wave;
(b) calculating the thickness of the layer based upon the measured energies of the steady state echo waves.

In its second aspect, the invention provides a method a method for detecting the thickness of a bone, in an organism the method comprising the steps of:
(a) for each of a plurality of frequencies $f_1, \ldots f_k$
  (aa) generating a continuous vibrational wave at a surface of the bone;
  (ab) measuring an energy of a steady state echo wave produced in the organism in response to the generated vibrational wave;
(b) calculating the thickness of the bone based upon the measured energies of the steady state echo waves.

In its third aspect, the invention provides a device for determining a thickness of a layer in an object, the device comprising:
(a) a transducer configured to generate a plurality of input vibrational wave pulses;
(b) a receiver configured to receive a steady-state echo wave produced by an input vibrational wave pulse;
(c) a probe configured to transmit a vibrational wave from the transducer to a surface of the bone and to transmit steady-state echo wave from the surface to the receiver;
(d) a processor configured to
  (da) determine a frequency of each of the plurality of input vibrational waves;
  (db) store in a memory an. energy of each of a plurality of steady-state echo waves; and
  (dc) calculate the thickness based upon the stored energies of the steady-state echo waves; and
(e) a display configured to display the thickness.

In its fourth aspect, the invention provides a device for determining a thickness of a bone in an organism, the device comprising:
(a) a transducer configured to generate a plurality of input vibrational wave pulses;
(b) a receiver configured to receive a steady-state echo wave produced by an input vibrational wave pulse;
(c) a probe configured to transmit a vibrational wave from the transducer to a surface of the bone and to transmit steady-state echo wave from the surface to the receiver;
(d) a processor configured to
  (da) determine a frequency of each of the plurality of input vibrational waves;
  (db) store in. a memory an energy of each of a plurality of steady-state echo waves; and
  (dc) calculate the thickness based upon the stored energies of the steady-state echo waves; and
(e) a display configured to display the thickness.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 2 shows the formation of a steady state echo from a layer in a multi-layer structure.

DETAILED DESCRIPTION OF A PREFERRED EMBODIMENT

Figure 1:
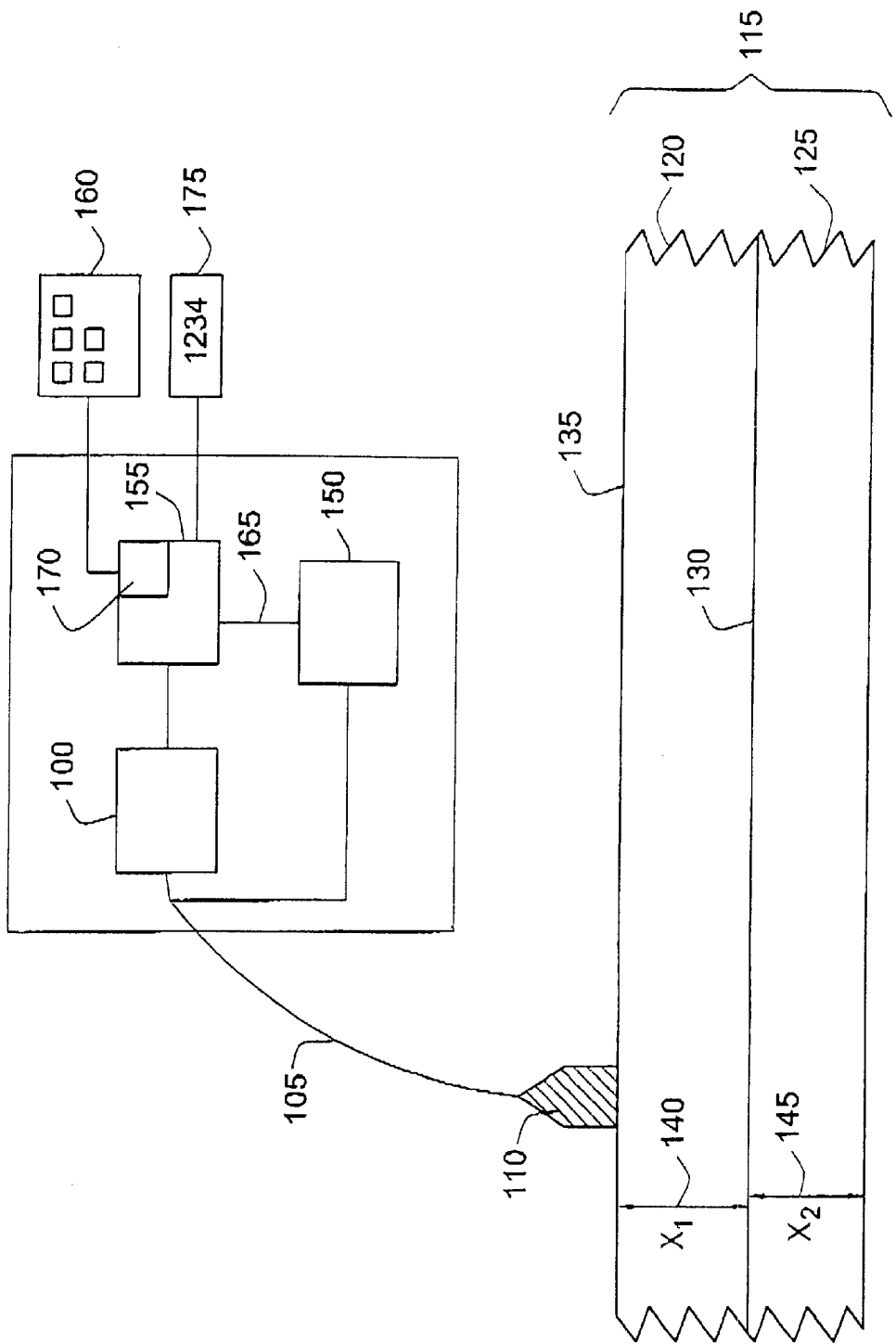
FIG. 1. is an apparatus for determining the thickness of a layer in accordance with one embodiment of the invention.

FIG. 1 shows an. embodiment of the invention in which an ultrasound transducer 100 is configured to generate a vibrational wave pulses of variable frequencies in a long flexible probe 105. The probe 105 is preferably made from a material having a high acoustic impedance ($Z_{in}$) such as metal. The probe 105 may also have a coating having a low acoustic coefficient (not shown). Distal end 110 of the probe 105 is configured to be applied onto a surface 135 of a multi-layer structure 115. The distal end 110 of the probe 105 is widened in order to increase the area of the contact between the distal end 110 of the probe 105.

The structure 115 consists of two or more layers, of which two, 120 and 125, are shown in FIG. 1. The layers 120 and 125 are in contact with each other at an interface 130. The layers 120 and 125 have unknown thicknesses $X_1$ and $X_2$, respectively, as indicated by arrows 140 and 145. The speed of sound in each of the layers 120 and 125, $C_1$ and $C_2$, respectively. are Flown and the acoustic impedance of each of the layers 120 and 125, $Z_1$ and $Z_2$, respectively are known to satisfy the relation $Z_{in} > Z_1 > Z_2$.

A processor 150 causes the transducer 100 to generate a series of vibrational probe waves of increasing frequency. At each frequency the ultrasound transducer 100 generates an input vibrational wave in probe 105. The frequency of the wave is determined by a processor 155. The probe 105 transmits the wave to the surface 135. FIG. 2 shows an enlargement of the distal end 110 of the probe 105. An is input wave 200 of a particular frequency arrives at the surface 135. At surf ace 135 some of the energy of the wave 200 is reflected from the surface 135 back into the probe 105, to form a first echo wave 205. The part of wave 200 transmitted into the layer 120, wave 210, continues through layer 120 until it reaches the interface 130. At the interface 130 some of the wave energy is reflected back from the interface 20 130 (wave 215), while some of the wave energy is transmitted into layer 125 (wave 220). The reflected wave 215 from the interface 130 travels back to surface 135 where part of the energy of the wave 215 is transmitted back into the probe 105 to form a second echo wave 225, and part of the energy is reflected back to the interface 130 (wave 230).

The wave 230 has the same fate as the wave 210, thus generating a third echo wave (not shown). Ultimately, a decaying sequence of echo waves is generated, the first and second of which are the waves 205 and 225. The steady-state echo wave 235 is the superimposition of all of the echo waves in the sequence. The steady-state echo wave is transmitted back along the probe 105 to a receiver 150 shown in FIG. 1. The receiver 150 produces a signal 165 indicative of the energy of the steady-state echo that is input to the processor 155 which stores the energy in a memory 170. The processor 155 causes the transducer to generate a series of vibrational wave pulses of increasing frequency. the energy of the steady-state echo wave is stored in the memory 170. The frequency range of the frequency increment between consecutive frequencies can. be input by a user by means of a keyboard 160.

It is known that the steady-state power transmission coefficient, $\alpha_t$ from the probe 105 through the layer $x_1$ and into the layer $x_2$ depends upon the frequency f of the input wave according to the equation;

$$\alpha_t = \frac{4Z_2 Z_{in}}{(Z_2 + Z_{in})^2 \cos^2 \frac{2\pi f x_1}{c} + \left(Z_1 + \frac{Z_2 Z_{in}}{Z_1}\right)^2 \sin^2 \frac{2\pi f x_1}{c}} \quad (1)$$

(see for example Kinsler, L.E. and Frey, A.R. Fundamentals of Acoustics, John Wiley & and Sons, 1950, p. 138, Equation 6.36)

In the case that $$Z_1 + \frac{Z_2 Z_{in}}{Z_1} \rangle Z_z + Z_{in}$$

$\alpha_t$ has maxima occurring at frequencies $f_n$ at which $$\frac{2\pi f_n}{c} x_1 = (2n-1)\frac{\pi}{2} \text{ for } n = 0, \pm 1, \pm 2, \ldots \quad (2)$$

from which it follows that $$f_n = \frac{(2n-1)c}{4x_1} \quad (3)$$

and $$x_1 = \frac{(2n-1)c}{4f_n} \quad (4)$$

In this case, the thickness $X_1$ of the layer 120 is calculated by the processor 155 as follows. The processor 155 searches for a predetermined number of consecutive frequencies $f_n, f_{n+1} \ldots f_{n+k}$ at which the energy of the steady-state echo has consecutive local minima corresponding to frequencies where $\alpha_t$ has a local maximum.

The processor then calculates the ratio of the consecutive pairs of minimal frequencies $$\frac{f_n}{f_{n+1}}, \frac{f_{n+1}}{f_{n+2}}, \ldots \frac{f_{n+k-1}}{f_{n+k}}$$

and then finds n by solving the over-determined system of equations:

$$\frac{f_n}{f_{n+1}} = \frac{2n-1}{2(n+1)-1}$$

$$\frac{f_{n+1}}{f_{n+2}} = \frac{2(n+1)-1}{2(n+2)-1}$$

$$\vdots$$

$$\frac{f_{n+k}}{f_{n+k+1}} = \frac{2(n+k)-1}{2(n+k+1)-1}$$

The processor then calculates $X_1$ from equation 4. The results of the calculation are displayed on a display 175. In the case that $$Z_z + Z_{in})Z_1 + \frac{Z_2 Z_{in}}{Z_1}$$

$\alpha_t$ has maxima occurring at frequencies $f_n$ at which, $$\frac{2\pi f_n}{c} x_1 = n\pi \text{ for } n = 0, \pm 1, \pm 2, \ldots \quad (2')$$

from which it follows that $$f_n = \frac{nc}{2x_1} \quad (3')$$

and

-continued $$x_1 = \frac{nc}{2f_n} \quad (4')$$

In this case, the thickness $X_1$ of the layer 120 is calculated by the processor 155 as follows. The processor 155 searches for a predetermined number of consecutive frequencies $f_n$, $f_{n+1} \ldots f_{n+k}$ at which the energy of the steady-state echo has consecutive local minima corresponding to frequencies where $\alpha_t$ has a local The processor then calculates the ratio of the consecutive pairs of minimal frequencies $$\frac{f_n}{f_{n+1}}, \frac{f_{n+1}}{f_{n+2}}, \ldots \frac{f_{n+k-1}}{f_{n+k}}$$

and then finds n by solving the over-determined system of equations:

$$\frac{f_n}{f_{n+1}} = \frac{n}{n+1}$$

$$\frac{f_{n+1}}{f_{n+2}} = \frac{n+1}{n+2}$$

$$\vdots$$

$$\frac{f_{n+k}}{f_{n+k+1}} = \frac{n+k}{n+k+1}$$

The processor then calculates $X_1$ from equation 4'. The results of the calculation are displayed on a display 175.

EXAMPLE

An initial frequency of the input wave 200 of $f_0=0.285$ MHz may be used. and the frequency varied with a frequency increment of 0.056 MHz. If it is found that three consecutive minima of the steady-state echo wave occur at frequencies of 1 $f_n=0.31$ MHz, $f_{n+1}=0.366$ MHz, $f_{n+2}=0.421$ MHz, then the calculated ratios are:

$$\frac{f_{n+1}}{f_n} = \frac{0.366}{0.31} = 1.1806$$

$$\frac{f_{n+2}}{f_{n+1}} = \frac{0.421}{0.366} = 1.1502$$

From these ratios the best fit is $n_1=6$. Using Equation (2), (with $c_1=3.36 \times 10^3$ m/sec.) the thickness $X_1$ is calculated to be 2.98 mm.

If it is found that three consecutive minima of the steady-state echo wave occur at frequencies of $f_n=4.69412$ MHz, $f_{n+2}=5.1882$ MHz and $f_{n+2}=5.682$ MHz.

Then the calculated ratios are $$\left(\frac{(2(N1+1)-1)}{(2(N1-1))}\right) = 1.1052, \text{ and } \frac{f_{n+1}}{f_n} = \frac{5.1882}{4.69412} = 1.1052$$

$$\left(\frac{(2(N1+2-1))}{(2(N1+1)-1)}\right) = 1.0952, \text{ and } \frac{f_{n+2}}{f_{n+1}} = \frac{5.682}{5.1882} = 1.0952.$$

The value of $n_1$ that best fits is $n_1=10$, and $X_1$ is calculated to be 0.34 mm.

What is claimed is:

1. A method for determining a thickness $x_1$ of a layer in an object, the method comprising the steps of:
  (a) for each of plurality of frequencies $f_1, \ldots f_k$
    (aa) generating a continuous vibrational wave at a surface of the layer;
    (ab) measuring an energy of a steady state echo wave produced in the object in response to the generated vibrational wave;
  (b) calculating the thickness of the layer based upon the measured energies of the steady state echo waves.

2. The method of claim 1, further comprising a step of determining two or more frequencies $f_{n1}, f_{n2}, \ldots f_{nj}$ among the frequencies $f_1 \ldots f_k$ at which the energy of the steady state echo wave has a local minimum.

3. The method of claim 2, wherein the thickness is calculated based upon the two or more frequencies $f_{n1}, f_{n2} \ldots f_{nj}$.

4. The method of claim 3, wherein the number of frequencies at which the energy of the steady-state echo has a local minimum between $f_{n1}$, and $f_{n1+1}$ is a constant m for all 1 between 1 and j-1.

5. The method according to claim 4, wherein the constant m is zero.

6. method of claim 4 wherein the thickness of the layer is calculated based upon the ratios $$\frac{f_{n2}}{f_{n1}}, \frac{f_{n3}}{f_{n2}} \ldots \frac{f_{nj}}{f_{nj-1}}.$$

7. The method of claim 6, wherein calculation of the thickness involves solving the over determined system of equations for $n_1$ $$\frac{f_{n2}}{f_{n1}} = \frac{2(n_1+m+1)-1}{2n_1-1}$$

$$\frac{f_{n3}}{f_{n2}} = \frac{2(n_1+2m+1)-1}{2(n_1+m+1)-1}$$

$$\vdots$$

$$\frac{f_{nj}}{f_{nj-1}} = \frac{2(n_1+(j-1)m)-1}{2(n_1+(j-2)m+1)-1}.$$

8. The method of claim 7, wherein the thickness $x_1$ is calculated according to the algorithmic expression:

$$x_1 = \frac{(2n_1-1)c}{4f_{n1}},$$

where c is a speed of the waves in the layer.

9. The method of claim 6, wherein calculation of the thickness involves solving the over determined system of equations for $n_1$ $$\frac{f_{n2}}{f_{n1}} = \frac{n_1+m+1}{n_1}$$

$$\frac{f_{n3}}{f_{n2}} = \frac{n_1+2m+1}{n_1+m+1}$$

$$\vdots$$

$$\frac{f_{nj}}{f_{nj-1}} = \frac{n_1+(j-1)m+1}{n_1+(j-2)m+1}.$$

10. The method of claim 9, wherein the thickness $x_1$ is calculated according to the algorithmic expression:

$x_1 n_1 c//2 f_{n1}$, where c is a speed of the waves in the layer.

11. A method for detecting the thickness of a bone, in an organism the method comprising the steps of:
- (a) for each of a plurality of frequencies $f_1, \ldots f_k$
  - (aa) generating a continuous vibrational wave at a surface of the bone;
  - (ab) measuring an energy of a steady state echo wave produced in the organism in response to the generated vibrational wave;
- (b) calculating the thickness of the bone based upon the measured energies of the steady state echo waves.

12. A device for determining a thickness of a layer in an object, the device comprising:
- (a) a transducer configured to generate a plurality of input vibrational wave pulses;
- (b) a receiver configured to receive a steady-state echo wave produced by an input vibrational wave pulse;
- (c) a probe configured to transmit a vibrational wave from the transducer to a surface of the layer and to transmit the steady-state echo wave from the surface to the receiver;
- (d) a processor configured to
  - (da) determine a frequency of each of the plurality of input vibrational waves;
  - (db) store in a memory an energy of each of a plurality of steady-state echo waves; and
  - (dc) calculate the thickness based upon the stored energies of the steady-state echo waves; and
- (e) a display configured to display the thickness.

13. The device according to claim 12, wherein the probe has an acoustic impedance $Z_{in}$ satisfying $Z_{in} > Z_i$, wherein $Z_i$ is an acoustic impedance of the layer.

14. The device according to claim 13, wherein $Z_{in}$ further satisfies $$Z_1 + \frac{Z_2 Z_{in}}{Z_1} \Big) Z_2 Z_{in},$$

wherein $Z_2$ is the acoustic impedance of a region of the object juxtaposed to the layers.

15. The device according to claim 13, wherein $Z_{in}$ further satisfies $$Z_2 + Z_{in}) Z_1 + \frac{Z_2 Z_{in}}{Z_1},$$

wherein $Z_2$ is the acoustic impedance of a region of the object juxtaposed to the layer.

16. A device for determining a thickness of a bone in an organism, the device comprising:
- (a) a transducer configured to generate a plurality of input vibrational wave pulses;
- (b) a receiver configured to receive a steady-state echo wave produced by an input vibrational wave pulse;
- (c) a probe configured to transmit a vibrational wave from the transducer to a surface of the bone and to transmit the steady-state echo wave from the surface to the receiver;
- (d) a processor configured to
  - (da) determine a frequency of each of the plurality of input vibrational waves;
  - (db) store in a memory an energy of each of a plurality of steady-state echo waves; and
  - (dc) calculate the thickness based upon the stored energies of the steady-state echo waves; and
- (e) a display configured to display the thickness.

* * * * *

UNITED STATES PATENT AND TRADEMARK OFFICE
CERTIFICATE OF CORRECTION

PATENT NO.    : 6,494,097 B1                                        Page 1 of 1
DATED         : December 17, 2002
INVENTOR(S)   : Shihadeh It is certified that error appears in the above-identified patent and that said Letters Patent is hereby corrected as shown below:

Column 6,
Line 22, before "method of claim 4", please insert -- The --.
Line 22, after "of claim 4" and before "wherein the", please insert -- , --.
Line 66, please replace "$x_1 n_1 c/12 f_{n1}$", with $$x_1 = \frac{n_1 c}{2 f_{n1}}$$

Signed and Sealed this

Eighth Day of April, 2003

JAMES E. ROGAN
*Director of the United States Patent and Trademark Office*